(12) United States Patent
Hirokawa et al.

(10) Patent No.: US 12,412,246 B2
(45) Date of Patent: Sep. 9, 2025

(54) IMAGE PROCESSING METHOD, IMAGE PROCESSING DEVICE, AND IMAGE PROCESSING PROGRAM

(71) Applicant: NIKON CORPORATION, Tokyo (JP)

(72) Inventors: Mariko Hirokawa, Yokohama (JP); Yasushi Tanabe, Fujisawa (JP)

(73) Assignee: NIKON CORPORATION, Tokyo (JP)

( * ) Notice: Subject to any disclaimer, the term of this patent is extended or adjusted under 35 U.S.C. 154(b) by 669 days.

(21) Appl. No.: 17/769,313

(22) PCT Filed: Oct. 17, 2019

(86) PCT No.: PCT/JP2019/040889
§ 371 (c)(1),
(2) Date: Aug. 30, 2022

(87) PCT Pub. No.: WO2021/075026
PCT Pub. Date: Apr. 22, 2021

(65) Prior Publication Data
US 2023/0139849 A1    May 4, 2023

(51) Int. Cl.
*G06T 5/50*    (2006.01)
*A61B 3/10*    (2006.01)
(Continued)

(52) U.S. Cl.
CPC .............. *G06T 5/50* (2013.01); *A61B 3/102* (2013.01); *A61B 3/1233* (2013.01);
(Continued)

(58) Field of Classification Search
CPC ... G06T 5/50; G06T 7/136; G06T 7/11; G06T 2207/10101; G06T 2207/20212;
(Continued)

(56) References Cited

U.S. PATENT DOCUMENTS

| 5,881,124 A | * | 3/1999 | Giger | G06T 7/0012 |
| | | | | 250/363.04 |
| 2002/0009215 A1 | * | 1/2002 | Armato, III | G06T 7/187 |
| | | | | 382/131 |

(Continued)

FOREIGN PATENT DOCUMENTS

| CN | 112004457 A | * | 11/2020 | ........... A61B 3/0025 |
| CN | 114828732 A | * | 7/2022 | ............... A61B 3/10 |

(Continued)

OTHER PUBLICATIONS

Office Action issued in corresponding Japanese Patent Application No. 2021-552060 dated May 23, 2023 (7 pages).
(Continued)

*Primary Examiner* — Pinalben Patel
(74) *Attorney, Agent, or Firm* — Foley & Lardner LLP

(57) ABSTRACT

An image processing method including acquiring a fundus image, extracting a first area including a first feature from the fundus image, extracting a second area including a second feature different from the first feature from the fundus image, and generating a combined image in which the extracted first area and the extracted second area are combined.

18 Claims, 12 Drawing Sheets

(51) Int. Cl.
*A61B 3/12* (2006.01)
*G06T 7/11* (2017.01)
*G06T 7/136* (2017.01)

(52) U.S. Cl.
CPC .............. *A61B 3/1241* (2013.01); *G06T 7/11* (2017.01); *G06T 7/136* (2017.01); *G06T 2207/10101* (2013.01); *G06T 2207/20212* (2013.01); *G06T 2207/30041* (2013.01); *G06T 2207/30101* (2013.01)

(58) Field of Classification Search
CPC . G06T 2207/30041; G06T 2207/30101; A61B 3/102; A61B 3/1233; A61B 3/1241
See application file for complete search history.

(56) References Cited

U.S. PATENT DOCUMENTS

| | | | | |
|---|---|---|---|---|
| 2010/0104148 | A1* | 4/2010 | Bovik | G06T 5/20 |
| | | | | 382/128 |
| 2011/0164219 | A1* | 7/2011 | Ono | A61B 3/12 |
| | | | | 351/206 |
| 2019/0139223 | A1* | 5/2019 | Nie | G06V 10/25 |
| 2021/0004939 | A1 | 1/2021 | Hirokawa | |

FOREIGN PATENT DOCUMENTS

| | | | | |
|---|---|---|---|---|
| CN | 118078205 A | * | 5/2024 | ........... A61B 3/0025 |
| CN | 118982519 A | * | 11/2024 | ........... G06T 7/0012 |
| WO | WO-2019/181981 A1 | | 9/2019 | |

OTHER PUBLICATIONS

Sonoda, Shozo, "Introducing Timelines to Imaging Analysis : Quantitative Analysis of Retinochoroidal Disease Using Imaging Technology", Journal of Japanese Ophthalmological Society) Mar. 10, 2019, vol. 123, No. 3, pp. 260-283, with partial translation (26 pages).

JP Notice of Reasons for Refusal issued in corresponding Japanese Application No. 2024-084261 Dated Dec. 10, 2024 (6 pages).

Shota Uruma et al., "Computerized extraction of vessel regions in retinal fundus images", vol. 111 No. 389, IEICE Technical Report, JAPAN, The Institute of Electronics, Information and Communication Engineers, 2012 (5 pages).

CN First Office Action issued in corresponding CN Application No. 201980102988.3 Dated Dec. 31, 2024 (20 pages).

JP Notice of Reasons of Refusal issued in corresponding Japanese Application No. 2024-084261 Dated May 7, 2025 (2 pages).

CN Office Action issued in corresponding CN Application No. 201980102988.3 Dated May 15, 2025 (23 pages).

* cited by examiner

FIG.9

IMAGE PROCESSING METHOD, IMAGE PROCESSING DEVICE, AND IMAGE PROCESSING PROGRAM

TECHNICAL FIELD

The technology disclosed herein relates to an image processing method, an image processing device, and an image processing program.

BACKGROUND ART

An optical coherence tomography instrument that makes a choroidal vascular network selectively visible is disclosed in the specification of U.S. Pat. No. 10,136,812. There is a desire for an image processing method for analyzing the choroidal vasculature.

SUMMARY OF INVENTION

An image processing method of a first aspect of technology disclosed herein includes acquiring a fundus image, extracting a first area including a first feature from the fundus image, extracting a second area including a second feature different from the first feature from the fundus image, and generating a combined image in which the extracted first area and the extracted second area are combined.

An image processing device of a second aspect of technology disclosed herein includes an image acquisition section configured to acquire a fundus image, a first extraction section configured to extract a line-shaped portion of vasculature from the fundus image, a second extraction section configured to extract a lump-shaped portion of vasculature from the fundus image, and a blood vessel visualizing section configured to integrate an image of the extracted line-shaped portion together with an image of the extracted lump-shaped portion to generate a vascular image in which blood vessels have been made visible.

A non-transitory storage medium storing an image processing program of a third aspect of technology disclosed herein causes a computer to function as an image acquisition section configured to acquire a fundus image, a first extraction section configured to extract a line-shaped portion of vasculature from the fundus image, a second extraction section configured to extract a lump-shaped portion of vasculature from the fundus image; and a blood vessel visualizing section configured to integrate an image of the extracted line-shaped portion together with an image of the extracted lump-shaped portion to generate a vascular image in which blood vessels have been made visible.

BRIEF DESCRIPTION OF DRAWINGS

FIG. 9 is a schematic diagram illustrating a display screen 500.

DESCRIPTION OF EMBODIMENTS

Detailed explanation follows regarding exemplary embodiments, with reference to the drawings.

Figure 1:
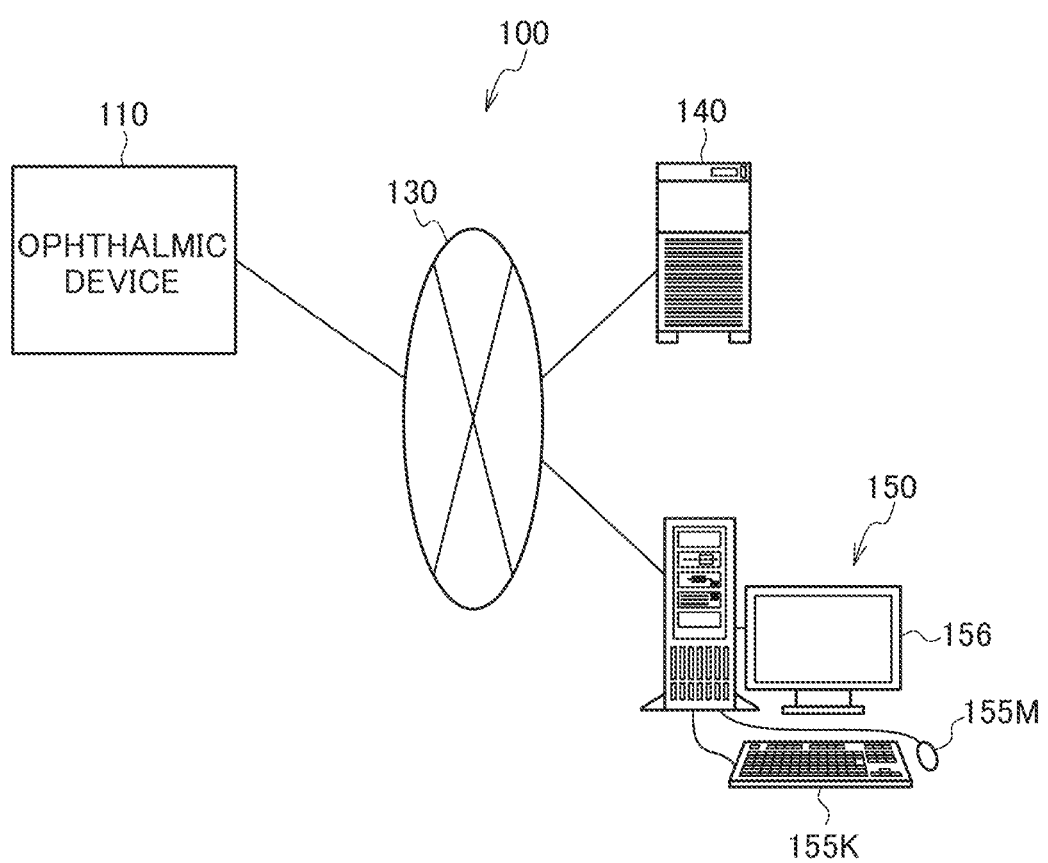
FIG. 1 is a block diagram of an ophthalmic system 100.

Explanation follows regarding a configuration of an ophthalmic system 100, with reference to FIG. 1. As illustrated in FIG. 1, the ophthalmic system 100 includes an ophthalmic device 110, a management server device (referred to hereafter as "management server") 140, and a display device (referred to hereafter as "viewer") 150. The ophthalmic device 110 acquires an image of the fundus. The management server 140 stores plural fundus images and eye axial lengths obtained by imaging the fundi of plural patients using the ophthalmic device 110 in association with patient IDs. The viewer 150 displays fundus images and analysis results acquired by the management server 140.

The viewer 150 includes a display 156 that displays the fundus images and analysis results acquired by the management server 140, and a mouse 155M and a keyboard 155K that are used for operation.

The ophthalmic device 110, the management server 140, and the viewer 150 are connected together through a network 130. The viewer 150 is a client in a client-server system, and plural such devices are connected together through a network. There may also be plural devices for the management server 140 connected through the network in order to provide system redundancy. Alternatively, if the ophthalmic device 110 is provided with image processing functionality and with the image viewing functionality of the viewer 150, then the fundus images may be acquired and image processing and image viewing performed with the ophthalmic device 110 in a standalone state. Moreover, if the management server 140 is provided with the image viewing functionality of the viewer 150, then the fundus images may be acquired and image processing and image viewing performed by a configuration of the ophthalmic device 110 and the management server 140.

Note that other ophthalmic equipment (examination equipment for measuring a field of view, measuring intraocular pressure, or the like) and/or a diagnostic support device that analyzes images using artificial intelligence (AI) may be connected to the ophthalmic device 110, the management server 140, and the viewer 150 over the network 130.

Figure 2:
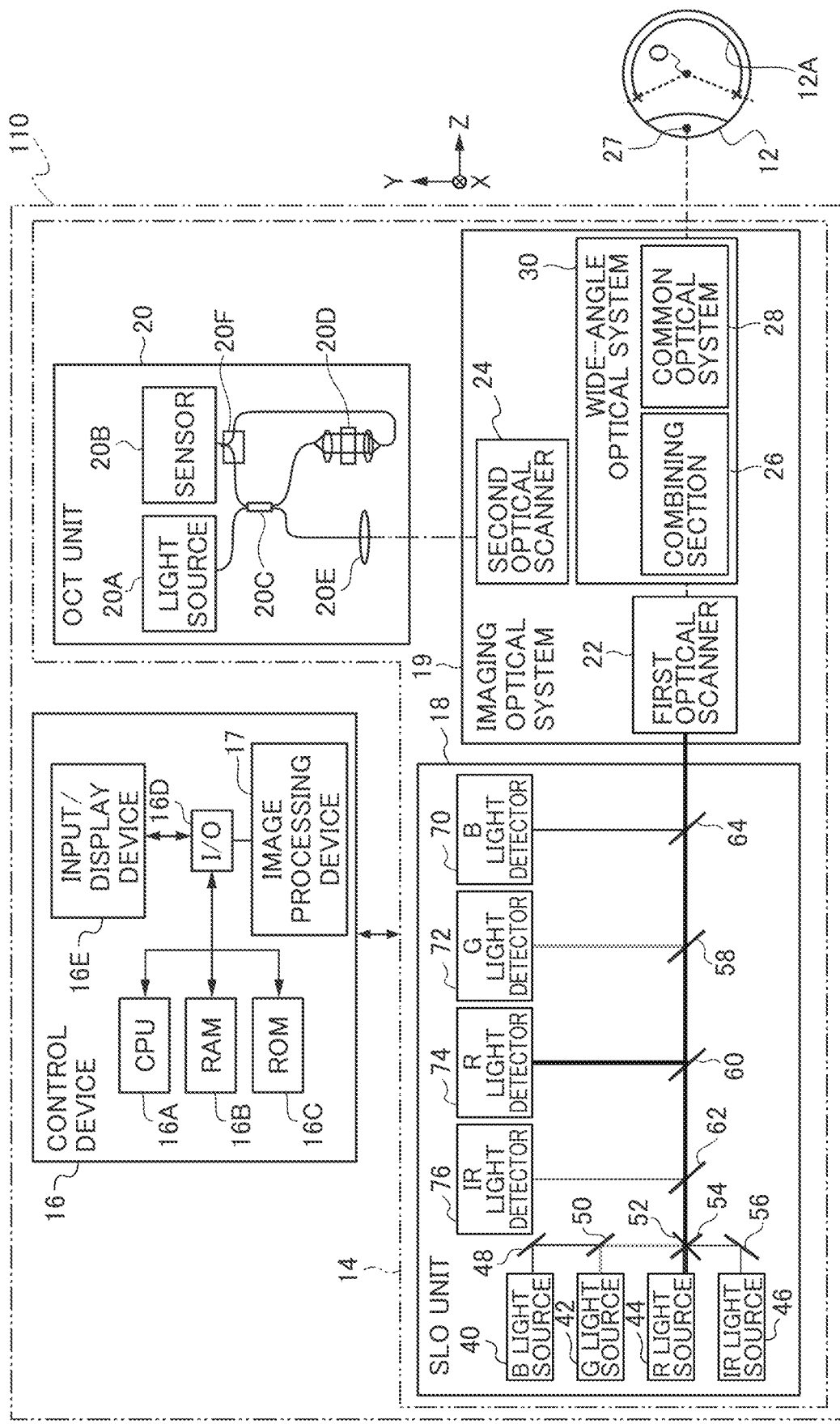
FIG. 2 is a schematic configuration diagram illustrating an overall configuration of an ophthalmic device 110.

Next, explanation follows regarding configuration of the ophthalmic device 110, with reference to FIG. 2. For ease of explanation, scanning laser ophthalmoscope is abbreviated to SLO. Optical coherence tomography is also abbreviated to OCT.

With the ophthalmic device 110 installed on a horizontal plane and a horizontal direction taken as an X direction, a direction perpendicular to the horizontal plane is denoted a Y direction, and a direction connecting the center of the pupil at the anterior eye portion of the examined eye 12 and the center of the eyeball is denoted a Z direction. The X direction, the Y direction, and the Z direction are thus mutually perpendicular directions.

The ophthalmic device 110 includes an imaging device 14 and a control device 16. The imaging device 14 is provided with an SLO unit 18, and an OCT unit 20, and acquires a fundus image of the fundus of the examined eye 12. Two-dimensional fundus images that have been acquired by the SLO unit 18 are referred to hereafter as SLO images. Tomographic images, face-on images (en-face images) and the like of the retina created based on OCT data acquired by the OCT unit 20 are referred to hereafter as OCT images.

The control device 16 includes a computer provided with a Central Processing Unit (CPU) 16A, Random Access Memory (RAM) 16B, Read-Only Memory (ROM) 16C, and an input/output (I/O) port 16D.

The control device 16 is provided with an input/display device 16E connected to the CPU 16A through the I/O port 16D. The input/display device 16E includes a graphical user interface to display images of the examined eye 12 and to receive various instructions from a user. An example of the graphical user interface is a touch panel display.

The control device 16 is also provided with an image processing device 17 connected to the I/O port 16D. The image processing device 17 generates images of the examined eye 12 based on data acquired by the imaging device 14. Note that the control device 16 is connected to the network 130 through a non-illustrated communication interface.

Although the control device 16 of the ophthalmic device 110 is provided with the input/display device 16E as illustrated in FIG. 2, the technology disclosed herein is not limited thereto. For example, a configuration may adopted in which the control device 16 of the ophthalmic device 110 is not provided with the input/display device 16E, and instead a separate input/display device is provided that is physically independent of the ophthalmic device 110. In such cases, the display device is provided with an image processing processor unit that operates under the control of the CPU 16A in the control device 16. Such an image processing processor unit may display SLO images and the like based on an image signal output as an instruction by the CPU 16A.

The imaging device 14 operates under the control of the CPU 16A of the control device 16. The imaging device 14 includes the SLO unit 18, an imaging optical system 19, and the OCT unit 20. The imaging optical system 19 includes a first optical scanner 22, a second optical scanner 24, and a wide-angle optical system 30.

The first optical scanner 22 scans light emitted from the SLO unit 18 two dimensionally in the X direction and the Y direction. The second optical scanner 24 scans light emitted from the OCT unit 20 two dimensionally in the X direction and the Y direction. As long as the first optical scanner 22 and the second optical scanner 24 are optical elements capable of deflecting light beams, they may be configured by any out of, for example, polygon mirrors, minor galvanometers, or the like. A combination thereof may also be employed.

The wide-angle optical system 30 includes an objective optical system (not illustrated in FIG. 2) provided with a common optical system 28, and a combining section 26 that combines light from the SLO unit 18 with light from the OCT unit 20.

The objective optical system of the common optical system 28 may be a reflection optical system employing a concave mirror such as an elliptical mirror, a refraction optical system employing a wide-angle lens, or may be a reflection-refraction optical system employing a combination of a concave minor and a lens. Employing a wide-angle optical system that utilizes an elliptical mirror, wide-angle lens, or the like enables imaging to be performed not only of a central portion of the fundus, but also of the retina at the periphery of the fundus.

For a system including an elliptical minor, a configuration may be adopted that utilizes an elliptical minor system as disclosed in International Publication (WO) Nos. 2016/103484 or 2016/103489. The disclosures of WO Nos. 2016/103484 and 2016/103489 are incorporated in their entirety by reference herein.

Observation of the fundus over a wide field of view (FOV) 12A is implemented by employing the wide-angle optical system 30. The FOV 12A refers to a range capable of being imaged by the imaging device 14. The FOV 12A may be expressed as a viewing angle. In the present exemplary embodiment the viewing angle may be defined in terms of an internal illumination angle and an external illumination angle. The external illumination angle is the angle of illumination by a light beam shone from the ophthalmic device 110 toward the examined eye 12, and is an angle of illumination defined with respect to a pupil 27. The internal illumination angle is the angle of illumination of a light beam shone onto the fundus F, and is an angle of illumination defined with respect to an eyeball center O. A correspondence relationship exists between the external illumination angle and the internal illumination angle. For example, an external illumination angle of 120° is equivalent to an internal illumination angle of approximately 160°. The internal illumination angle in the present exemplary embodiment is 200°.

SLO fundus images obtained by imaging at an imaging angle having an internal illumination angle of 160° or greater are referred to as UWF-SLO fundus images. UWF is an abbreviation of ultra-wide field (ultra-wide angled).

An SLO system is realized by the control device 16, the SLO unit 18, and the imaging optical system 19 as illustrated in FIG. 2. The SLO system is provided with the wide-angle optical system 30, enabling fundus imaging over the wide FOV 12A.

The SLO unit 18 is provided with a blue (B) light source 40, a green (G) light source 42, a red (R) light source 44, an infrared (for example near infrared) (IR) light source 46, and optical systems 48, 50, 52, 54, 56 to guide the light from the light sources 40, 42, 44, 46 onto a single optical path using reflection or transmission. The optical systems 48, 50, 56 are configured by mirrors, and the optical systems 52, 54 are configured by beam splitters. B light is reflected by the optical system 48, is transmitted through the optical system 50, and is reflected by the optical system 54. G light is reflected by the optical systems 50, 54, R light is transmitted through the optical systems 52, 54, and IR light is reflected by the optical systems 52, 56. The respective lights are thereby guided onto a single optical path.

The SLO unit 18 is configured so as to be capable of switching between the light source or the combination of light sources employed for emitting laser light of different wavelengths, such as a mode in which G light, R light and B light are emitted, a mode in which infrared light is emitted, etc. Although the example in FIG. 2 includes four light sources, i.e. the B light source 40, the G light source 42, the R light source 44, and the IR light source 46, the technology disclosed herein is not limited thereto. For example, the SLO unit 18 may, furthermore, also include a white light source, in a configuration in which light is emitted in various modes, such as a mode in which white light is emitted alone.

Light introduced to the imaging optical system 19 from the SLO unit 18 is scanned in the X direction and the Y direction by the first optical scanner 22. The scanning light passes through the wide-angle optical system 30 and the pupil 27 and is shone onto the posterior eye portion (fundus) of the examined eye 12. Reflected light that has been reflected by the fundus passes through the wide-angle optical system 30 and the first optical scanner 22 and is introduced into the SLO unit 18.

The SLO unit 18 is provided with a beam splitter 64 that, from out of the light coming from the posterior eye portion (fundus) of the examined eye 12, reflects the B light therein and transmits light other than B light therein, and a beam splitter 58 that, from out of the light transmitted by the beam splitter 64, reflects the G light therein and transmits light other than G light therein. The SLO unit 18 is further provided with a beam splitter 60 that, from out of the light transmitted through the beam splitter 58, reflects R light therein and transmits light other than R light therein. The SLO unit 18 is further provided with a beam splitter 62 that reflects IR light from out of the light transmitted through the beam splitter 60. The SLO unit 18 includes a B light detector 70 for detecting B light reflected by the beam splitter 64, and a G light detector 72 for detecting G light reflected by the beam splitter 58. The SLO unit 18 includes an R light detector 74 for detecting R light reflected by the beam splitter 60 and an IR light detector 76 for detecting IR light reflected by the beam splitter 62.

Light that has passed through the wide-angle optical system 30 and the scanner 22 and been introduced into the SLO unit 18 (i.e. reflected light that has been reflected by the fundus) is reflected by the beam splitter 64 and photo-detected by the B light detector 70 when B light, and is transmitted through the beam splitter 64 and reflected by the beam splitter 58 and photo-detected by the G light detector 72 when G light. When R light, the incident light is transmitted through the beam splitters 64, 58, reflected by the beam splitter 60, and photo-detected by the R light detector 74. When IR light, the incident light is transmitted through the beam splitters 64, 58, 60, reflected by the beam splitter 62, and photo-detected by the IR light detector 76. The image processing device 17 that operates under the control of the CPU 16A employs signals detected by the B light detector 70, the G light detector 72, the R light detector 74, and the IR light detector 76 to generate UWF-SLO images. Examples of the B light detector 70, the G light detector 72, the R light detector 74, and the IR light detector 76 include, for example, photodiodes (PDs) and avalanche photodiodes (APDs). The B light detector 70, the G light detector 72, the R light detector 74, and the IR light detector 76 correspond to the "image acquisition section" of technology disclosed herein. In the SLO unit 18, light returning after being reflected (scattered) by the fundus subject arrives at the light detectors through the first optical scanner 22, and always returns to the same position, namely the positions where the B light detector 70, the G light detector 72, the R light detector 74, and the IR light detector 76 are present. The light detectors accordingly do not need to be of a flat planar shape (two dimensional) configuration such as an area sensor, and detectors of a point shape (zero dimensional) configuration such as a PD or APD are optimal as the light detectors in the present exemplary embodiment. However, there is no limit to being a PD, APD, or the like, and a line sensor (one dimension) or an area sensor (two dimensions) may be employed.

The UWF-SLO image encompasses a UWF-SLO image (green fundus image) obtained by imaging the fundus in green, and a UWF-SLO image (red fundus image) obtained by imaging the fundus in red. The UWF-SLO image further encompasses a UWF-SLO image (blue fundus image) obtained by imaging the fundus in blue, and a UWF-SLO image (IR fundus image) obtained by imaging the fundus in IR.

The control device 16 also controls the light sources 40, 42, 44 so as to emit light at the same time. A green fundus image and a red fundus image, and a blue fundus image are obtained with mutually corresponding positions by imaging the fundus of the examined eye 12 at the same time with the B light, G light, and R light. An RGB color fundus image is obtained from the green fundus image, the red fundus image, and the blue fundus image. The control device 16 obtains a green fundus image and a red fundus image with mutually corresponding positions by controlling the light sources 42, 44 so as to emit light at the same time and by imaging the fundus of the examined eye 12 at the same time with the G light and R light. An RG color fundus image is obtained by mixing the green fundus image and the red fundus image together at a specific mixing ratio.

The UWF-SLO images further include an UWF-SLO image (video) imaged using ICG fluoroscopy. When indocyanine green (ICG) is injected into a blood vessel so as to reach the fundus, the indocyanine green (ICG) first reaches the retina, then reaches the choroid, before passing through the choroid. The UWF-SLO image (video) is a video image from the time the indocyanine green (ICG) injected into a blood vessel reached the retina until after passing through the choroid.

Image data of the blue fundus image, the green fundus image, the red fundus image, the IR fundus image, the RGB color fundus image, the RG color fundus image, and the UWF-SLO image is transmitted from the ophthalmic device 110 to the management server 140 through a non-illustrated communication IF.

An OCT system is realized by the control device 16, the OCT unit 20, and the imaging optical system 19 illustrated in FIG. 2. The OCT system is provided with the wide-angle optical system 30. This enables fundus imaging to be performed over the wide FOV 12A similarly to when imaging the SLO fundus images as described above. The OCT unit 20 includes a light source 20A, a sensor (detector) 20B, a first light coupler 20C, a reference optical system 20D, a collimator lens 20E, and a second light coupler 20F.

Light emitted from the light source 20A is split by the first light coupler 20C. After one part of the split light has been collimated by the collimator lens 20E into parallel light, to serve as measurement light, the parallel light is introduced into the imaging optical system 19. The measurement light is scanned in the X direction and the Y direction by the second optical scanner 24. The scanning light is shone onto the fundus through the wide-angle optical system 30 and the pupil 27. Measurement light that has been reflected by the fundus passes through the wide-angle optical system 30 and the second optical scanner 24 so as to be introduced into the OCT unit 20. The measurement light then passes through the collimator lens 20E and the first light coupler 20C before being incident to the second light coupler 20F.

The other part of the light emitted from the light source 20A and split by the first light coupler 20C is introduced into the reference optical system 20D as reference light, and is made incident to the second light coupler 20F through the reference optical system 20D.

The respective lights that are incident to the second light coupler 20F, namely the measurement light reflected by the fundus and the reference light, interfere with each other in the second light coupler 20F so as to generate interference light. The interference light is photo-detected by the sensor 20B. The image processing device 17 operating under the control of an image processing control section 206 generates OCT images, such as tomographic images and en-face images, based on OCT data detected by the sensor 20B.

OCT fundus images obtained by imaging at an imaging angle having an internal illumination angle of 160° or greater are referred to as UWF-OCT images.

The image data of the UWF-OCT images is sent from the ophthalmic device 110 to the management server 140 though the non-illustrated communication IF and is stored in a storage device 254.

Note that although in the present exemplary embodiment an example is given in which the light source 20A is a swept-source OCT (SS-OCT), the light source 20A may be configured from various types of OCT system, such as a spectral-domain OCT (SD-OCT) or a time-domain OCT (TD-OCT) system.

Figure 3:
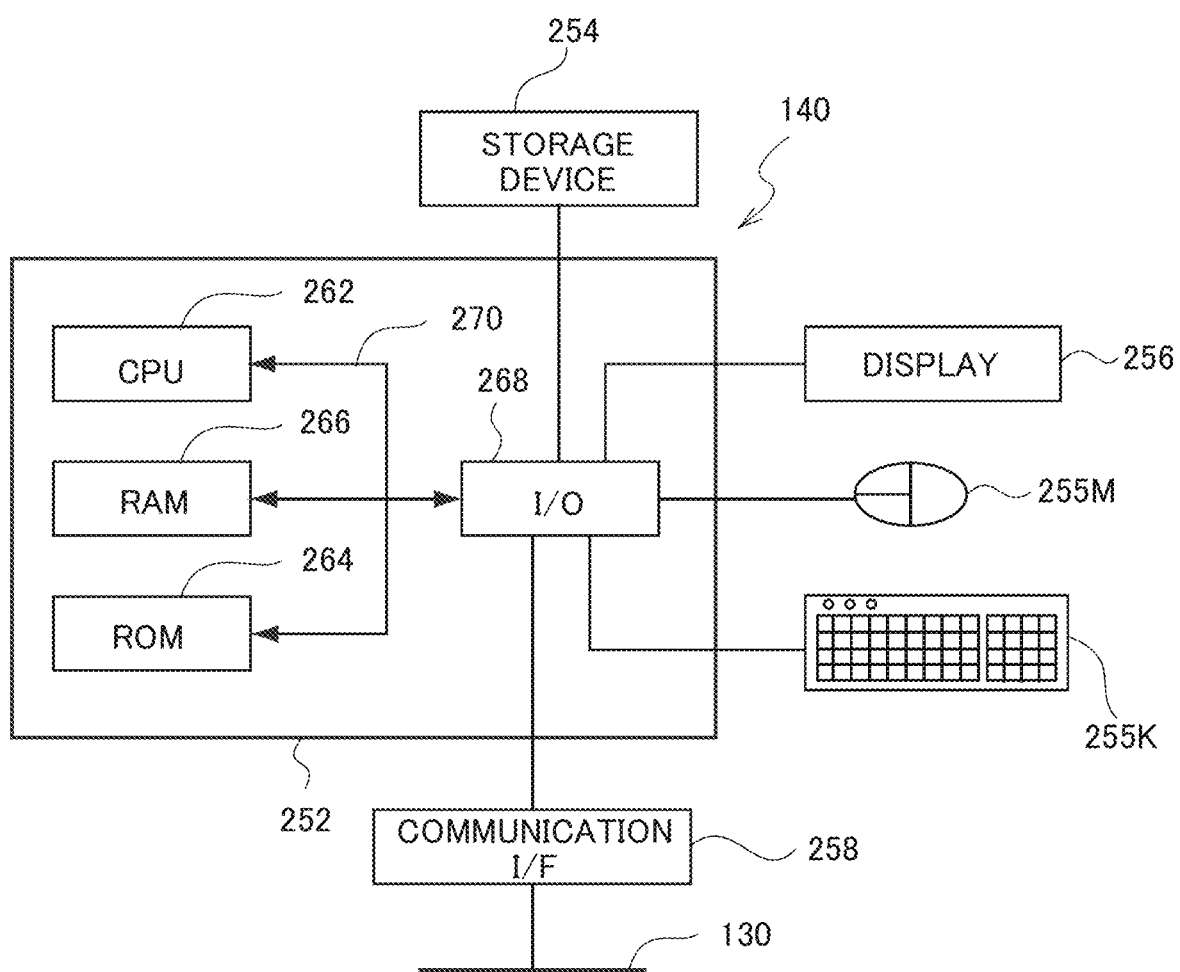
FIG. 3 is a block diagram of configuration of an electrical system of a management server 140.

Explanation follows regarding a configuration of an electrical system of the management server 140, with reference to FIG. 3. As illustrated in FIG. 3, the management server 140 is provided with a computer body 252. The computer body 252 includes a CPU 262, RAM 266, ROM 264, and an input/output (I/O) port 268. The storage device 254, a display 256, a mouse 255M, a keyboard 255K, and a communication interface (I/F) 258 are connected to the input/output (I/O) port 268. The storage device 254 is, for example, configured by non-volatile memory. The input/output (I/O) port 268 is connected to the network 130 through the communication interface (I/F) 258. The management server 140 is thus capable of communicating with the ophthalmic device 110 and the viewer 150. The storage device 254 is stored with an image processing program, described later. Note that the image processing program may be stored in the ROM 264.

The management server 140 stores respective data received from the ophthalmic device 110 in the storage device 254.

Figure 4:
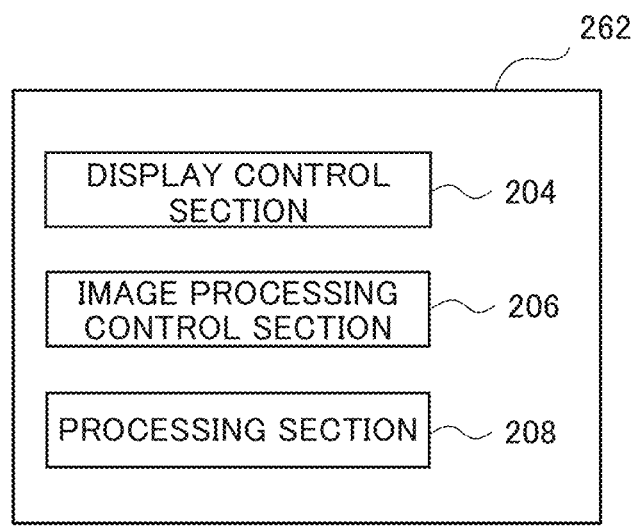
FIG. 4 is a block diagram illustrating functionality of a CPU 262 of a management server 140.

Next, description follows regarding various functions implemented by the CPU 262 of the management server 140 executing the image processing program, with reference to FIG. 4. The image processing program includes a display control function, an image processing control function and a processing function. By the CPU 262 executing the image processing program including each of these functions, the CPU 262 functions as a display control section 204, the image processing control section 206, and a processing section 208, as illustrated in FIG. 4.

The image processing control section 206 corresponds to a "first extraction section", "second extraction section", "blood vessel visualizing section", and "choroidal vascular image generation section" of technology disclosed herein.

Figure 5:
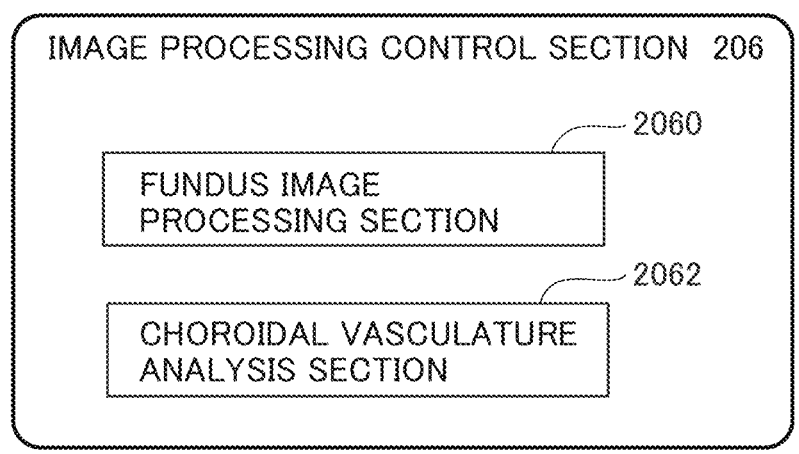
FIG. 5 is a block diagram illustrating functionality of an image processing control section 206 of a CPU 262 of a management server 140.

Next, description follows regarding various functions of the image processing control section 206, with reference to FIG. 5. The image processing control section 206 includes the functionality of a fundus image processing section 2060 that performs image processing such as generating sharpened images of the choroidal vasculature and the like from the fundus image, and a choroidal vasculature analysis section 2062 that performs image processing such as extracting line shaped portions and bulge portions (lump shaped portions) of the choroid. The line shaped portions correspond to a "first feature" of technology disclosed herein, and the bulge portions correspond to a "second feature" of technology disclosed herein.

Figure 6:
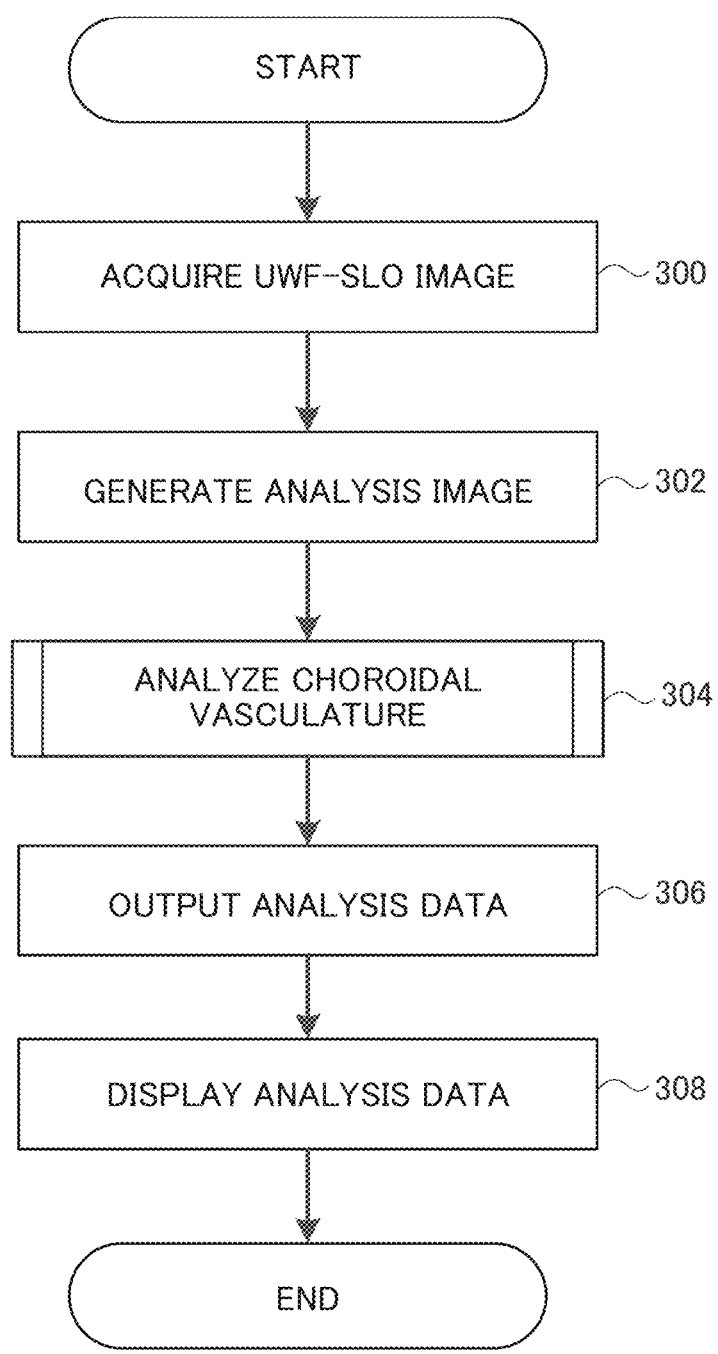
FIG. 6 is a flowchart of an image processing program.

Detailed explanation now follows regarding image processing by the management server 140, with reference to FIG. 6. Image processing (an image processing method) illustrated by the flowchart in FIG. 6 is implemented by the CPU 262 of the management server 140 executing an image processing program.

At step 300 the image processing control section 206 acquires the UWF-SLO images from the storage device 254. At step 302 the image processing control section 206 creates a choroidal vascular image in which the choroidal vasculature has been extracted from the acquired UWF-SLO images (red fundus image and green fundus image). Since red light is of longer wavelength, red light passes through the retina and reaches the choroid. The red fundus image therefore includes information relating to blood vessels present within the retina (retinal blood vessels) and information relating to blood vessels present within the choroid (choroidal vasculature). In contrast thereto, due to green light being of shorter wavelength than red light, green light only reaches as far as the retina. The green fundus image accordingly only includes information relating to the blood vessels present within the retina (retinal blood vessels). This thereby enables a choroidal vascular image CLA to be obtained by extracting the retinal blood vessels from the green fundus image and removing the retinal blood vessels from the red fundus image. The red fundus image corresponds to a "red-light capture image" of technology disclosed herein.

An explanation now follows regarding specific processing executed by the image processing control section 206 at step 302.

First, the image processing control section 206 performs de-noise processing to remove noise from each of the green fundus image and the red fundus image. A median filter or the like may be applied to remove noise.

The image processing control section 206 performs black hat filter processing to the green fundus image after noise removal to extract the retinal blood vessels from the green fundus image.

Next the image processing control section 206 removes the retinal blood vessels from the red fundus image by performing in-painting processing thereon using the retinal blood vessel position information extracted from the green fundus image to infill the retinal vasculature structure of the red fundus image with the same values as those of surrounding pixels. This processing generates an image in which the retinal blood vessels have been removed from the red fundus image and only the choroidal vasculature is made visible.

Next the image processing control section 206 removes low frequency components from the red fundus image after in-painting processing. Any well-known type of image processing for removing the low frequency components may be applied therefor, such as frequency filtering and spatial filtering.

Figure 12:
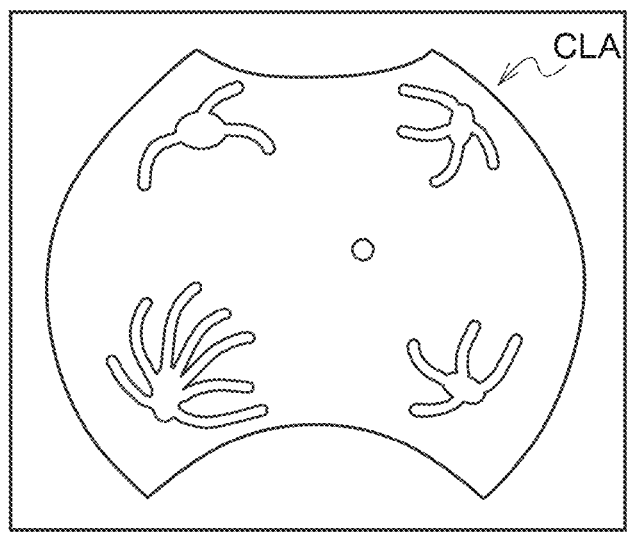
FIG. 12 is a diagram illustrating a choroidal vascular image CLA.

Then finally, the image processing control section 206 emphasizes the choroidal vasculature in the red fundus image by performing contrast limited adaptive histogram equalization processing on the image data of the red fundus image including the choroidal blood vessels that remain after the retinal blood vessels have been removed. The choroidal vascular image CLA illustrated in FIG. 12 is created by performing one cycle of the processing of step 302. The created choroidal vascular image CLA is stored in the storage device 254.

In the example described above the choroidal vascular image CLA is generated from the red fundus image and the green fundus image. However, there is no limitation thereto, and the image processing control section 206 may generate the choroidal vascular image CLA from a green fundus image and an IR fundus image. Moreover, the image processing control section 206 may generate the choroidal vascular image CLA from a blue fundus image and either a red fundus image or an IR fundus image.

Furthermore, the choroidal vascular image CLA may be generated from a UWF-SLO image (video) 510. The UWF-SLO image (video) 510 is, as described above, a video image from when indocyanine green (ICG) injected into a blood vessel reached the retina until after passing through the choroid. The choroidal vascular image CLA may be generated from a video image over the period of time from when the indocyanine green (ICG) passed through the retina until passing through the choroid.

Choroidal vasculature analysis processing is executed at step 304 to analyze the choroidal vasculature by independently performing extraction processing of the line shaped portions of the choroidal vasculature and extraction processing of the bulge portions thereof. Positions of vortex veins that are part of the choroidal vasculature are extracted from the extracted line shaped portions and bulge portions. The vortex veins are, anatomically, blood vessel sites where there is a concentration of choroidal blood vessels, and are the discharge paths for blood fluid that has flowed into the eyeball. The vortex veins are part of the choroidal vasculature, and there are from three to seven vortex veins present in the eyeball, present at fundus peripheral portion (in the vicinity of an equatorial portion of the eyeball). The vortex vein positions are recognized by performing image recognition on a fundus image, and have a lump shaped center portion with plural line shaped portions connected to the lump shaped center portion.

The choroidal vasculature analysis of step 304 is described in detail later.

At step 306, analysis data obtained by the choroidal vasculature analysis processing of step 304 is output to the storage device 254 of the management server 140. At step 308, the display control section 204 generates a display screen 500, described later and including an image of the extracted choroidal vasculature and also reflecting patient attribute information (patient name, age, information as to whether each fundus image is from the right eye or left eye, eye axial length, visual acuity, imaging date/time, etc.) corresponding to the patient ID. The display control section 204 then displays the display screen 500 on the display 256 of the management server 140, and ends processing.

The display screen 500 is stored in the storage device 254 of the management server 140. The display screen 500 stored in the storage device 254 of the management server 140 is transmitted to the viewer 150 according to operation from the viewer 150, and is output in a state enabling viewing on the display 156 of the viewer 150.

The processing illustrated in FIG. 6 may be executed by the CPU 16A provided to the control device 16 of the ophthalmic device 110. In cases in which this processing is executed by the CPU 16A of the ophthalmic device 110, along with display of the display screen 500 on the display of an ophthalmic device, the display screen 500 is also stored on a storage device of the management server 140.

The processing illustrated in FIG. 6 may be executed by a CPU provided to the viewer 150. In cases in which this processing is executed by a CPU of the viewer 150, along with display of the display screen 500 on the display 156 of the viewer 150, the display screen 500 is also stored on a storage device of the viewer 150 and on a storage device of the management server 140.

Figure 7:
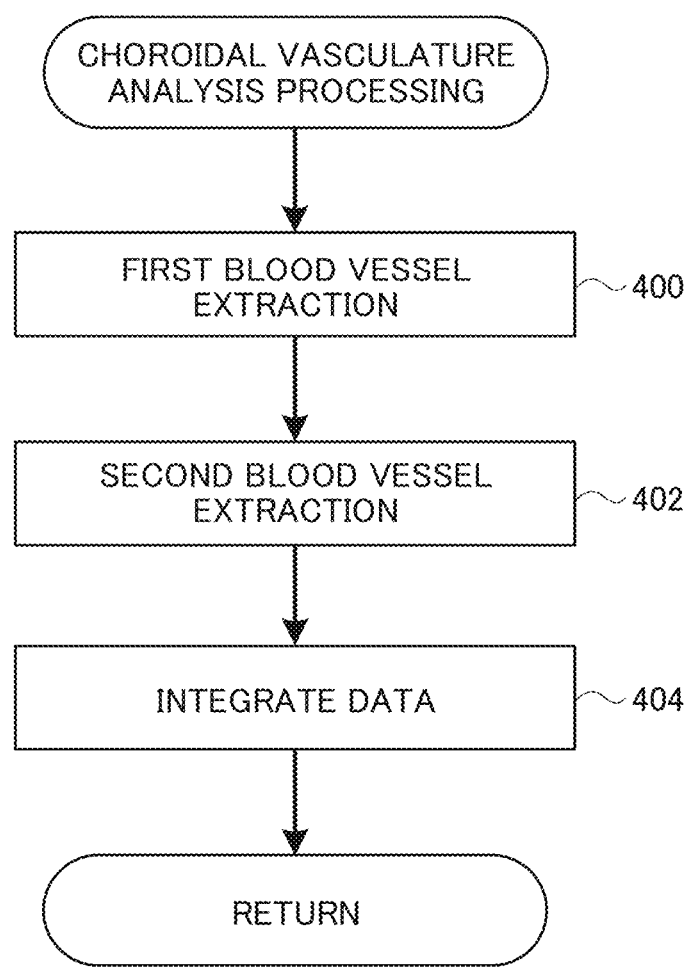
FIG. 7 is a flowchart of choroidal vasculature analysis processing of step 304 of FIG. 6.

FIG. 7 is a flowchart illustrating details regarding the choroidal vasculature analysis processing (step 304) illustrated in FIG. 6. At step 400, first blood vessel extraction processing is performed to extract line shaped portions from the choroidal vascular image CLA. At step 400, first, line emphasis processing is performed on the analysis image that is the choroidal vascular image CLA illustrated in FIG. 12. Choroidal blood vessels of line shape is emphasized by this line emphasis processing. The line emphasized image is then subjected to binarization processing. Next, image processing is performed to extract the line shaped portions from the line emphasized choroidal vascular image CLA.

The line emphasis processing is, for example, processing to emphasize line shaped structures by Hessian analysis using a Hessian matrix. The Hessian analysis discriminates as to whether a local structure in an image is a point, a line, or a plane by analyzing the eigenvalues of the Hessian matrix having elements of second order partial derivative coefficients computed using a second order derivative kernel for a specific filter such as a Gaussian kernel.

In the emphasis of the line shaped portions of the choroidal vasculature, in addition to the line emphasis processing described above, a Gabor filter may be employed to extract the orientation of an outline contained in the image, or a graph cut filter may be employed to extract by cutting the line shaped portions from the other portions. Moreover, edge emphasis processing may be employed such as a Laplacian filter or an unsharp mask.

Figure 8A:
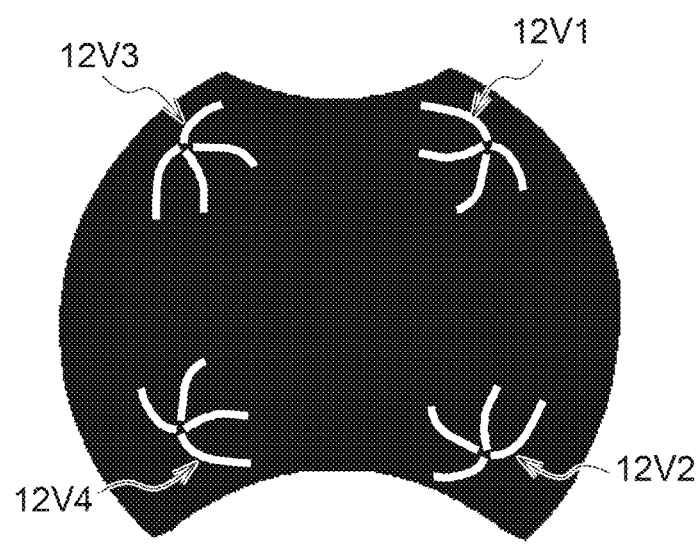
FIG. 8A is a schematic diagram illustrating an example of extracted line shaped portions 12V1, 12V2, 12V3, 12V4 of choroidal vasculature.

The line shaped portions of the choroidal vasculature are extracted as illustrated in FIG. 8A by the first blood vessel extraction processing of step 400. In FIG. 8A, the line shaped portions 12V1, 12V2, 12V3, 12V4 are displayed clearly distinct from other areas of the fundus.

At step 402, second blood vessel extraction processing is performed to extract bulge portions of the choroidal vasculature from the choroidal vascular image CLA. The second blood vessel extraction processing is performed by first binarizing the analysis image. Then areas of a specific number of contiguous white pixels are extracted from the binarized choroidal vascular image CLA as choroidal vasculature bulge portions. The specific number or area size is a number preset from a size of vortex veins (from standard data or the like for the choroid). This extraction processing may be performed by Hessian analysis using a Hessian matrix to detect concave and convex parts of an image, with the convex portions extracted as bulge portions. Hessian analysis corresponds to an "image processing filter that extracts the lump shaped portion alone" of technology disclosed herein.

Sometimes line shaped portions of the choroidal vasculature are also extracted together with pixels corresponding to the bulge portions. However, the line shaped portions and the bulge portions are integrated together by data integration processing described later, and so this does not affect the extraction of vortex vein positions.

Figure 8B:
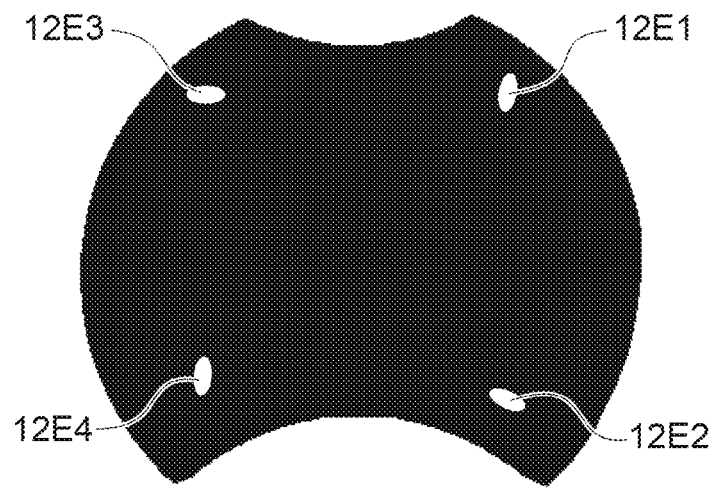
FIG. 8B is a schematic diagram illustrating an example of extracted bulge portions 12E1, 12E2, 12E3, 12E4 of choroidal vasculature.

The bulge portions of the choroidal vasculature are extracted as illustrated in FIG. 8B by the second blood vessel extraction processing at step 402. FIG. 8B illustrates an example of a case in which there are four vortex veins present in the eyeball (there are normally from four to six present), and the bulge portions 12E1, 12E2, 12E3, 12E4 are displayed so as to be clearly distinct from the other regions of the fundus. The bulge portions 12E1, 12E2, 12E3, 12E4 may be called inflow locations to the sclera side of the vortex veins present in the fundus peripheral portion (inlets of the choroid side of the vortex veins that run toward the outside of the eyeball). The choroidal bulge portions that were not able to be extracted by the line shaped portion extraction processing using the first blood vessel extraction processing of step 400 are able to be extracted by the binarization processing performed on the entire choroidal vascular image CLA at step 402.

Note that the second blood vessel extraction processing may be performed at step 400 and the first blood vessel extraction processing may be performed at step 402 by switching the sequence in the flowchart of FIG. 7 of the first blood vessel extraction processing and the second blood vessel extraction processing. This is because the first blood vessel extraction processing and the second blood vessel extraction processing are each independent processing unrelated to each other.

Figure 8C:
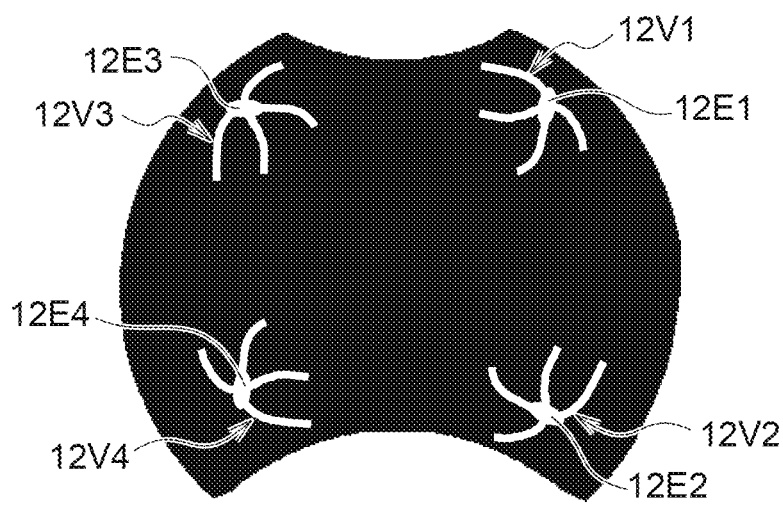
FIG. 8C is a schematic diagram illustrating a case in which line shaped portions 12V1, 12V2, 12V3, 12V4 of choroidal vasculature have been joined to bulge portions 12E1, 12E2, 12E3, 12E4 of choroidal vasculature.

As illustrated in FIG. 8C, at step 404 data integration is performed to integrate the line shaped portions resulting from the first blood vessel extraction processing and the bulge portions resulting from the second blood vessel extraction processing. In other words, a line shaped portion image of the extracted line shaped portions obtained at step 400 is combined with a bulge portion image of the extracted bulge portions obtained at step 402, so as to generate a single choroidal vascular image. Processing then proceeds to step 306 of FIG. 7, and processing to analyze the combined image is started. The choroidal vascular image illustrated in FIG. 8C corresponds to the "combined image" of technology disclosed herein.

FIG. 8C is a display of a joined state of the line shaped portions 12V1, 12V2, 12V3, 12V4 with the respective bulge portions 12E1, 12E2, 12E3, 12E4. Note that in each of FIGS. 8A, FIG. 8B, FIG. 8C, a background image where the fundus is not displayed is depicted in white, and an image of extracted choroidal vasculature, which is a binarized image, is clearly displayed, however, the outline between the binarized image and the background image may alone be depicted in white as long as it is possible to clearly see the binarized image. In the display screen 500 described later, a case is illustrated in which the background image, which is a region where the fundus is not being displayed, is depicted in white.

Figure 9:
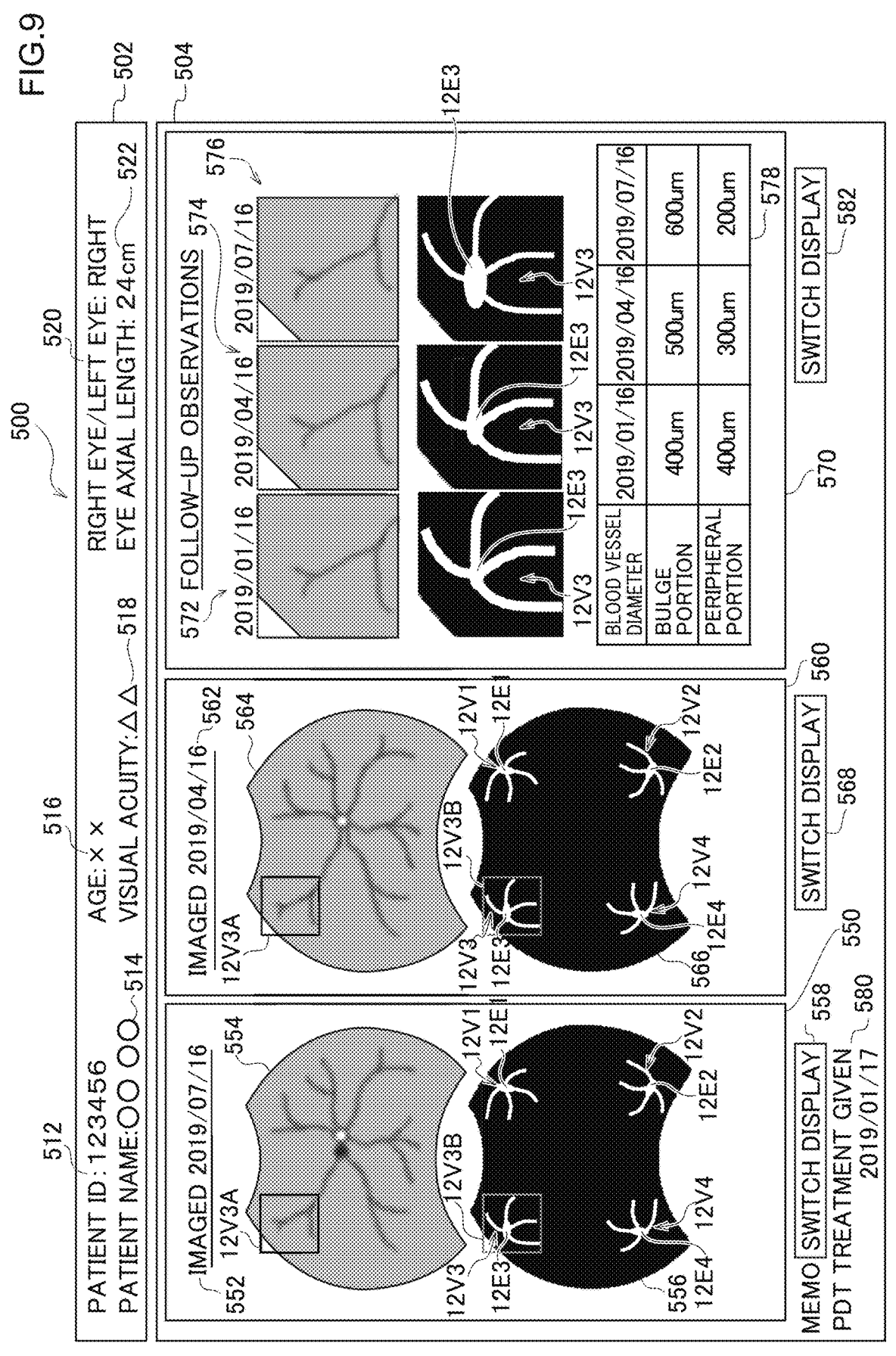

FIG. 9 is a schematic diagram illustrating the display screen 500 displayed on the display 256 of the management server 140 or the like. In addition to being displayed on the display 256 of the management server 140, the display screen 500 may also be displayed on the display 156 of the viewer 150, and may be displayed on the input/display device 16E of the ophthalmic device 110.

The display screen 500 includes an information display area 502 and an image display area 504, as illustrated in FIG. 9. The information display area 502 includes a patient ID display field 512, a patient name display field 514, an age display field 516, a visual acuity display field 518, a right eye/left eye display field 520, and an eye axial length display field 522.

The image display area 504 includes a latest image display field 550 to display the latest image (the fundus image imaged on Jul. 16, 2019 in FIG. 9), a previous image display field 560 to display an image imaged before the latest image (the fundus image imaged on Apr. 16, 2019 in FIG. 9), a follow-up observation field 570 to display changes by a time series of the fundus, and a remarks field 580 to display a treatment and a diagnostic memo or the like input by a user. There is an imaging date display field 552 at the top of the latest image display field 550 where a RG color fundus image 554 and a choroidal vasculature extraction image 556, which is a binarized image in which the line shaped portions 12V1, 12V2, 12V3, 12V4 of the choroidal vasculature are joined to the bulge portions 12E1, 12E2, 12E3, 12E4 of the choroidal vasculature, are displayed.

The previous image display field 560 includes an imaging date display field 562 at the top with an RG color fundus image 564 and a choroidal vasculature extraction image 566, which is a binarized image in which the line shaped portions 12V1, 12V2, 12V3, 12V4 are joined to the bulge portions 12E1, 12E2, 12E3, 12E4 of the choroidal vasculature, displayed therein.

The latest image display field 550 and the previous image display field 560 may each display a choroidal vasculature contrast image (ICG) and an optical coherence tomography angiogram (OCTA) instead of the RG color fundus images 554, 564 and the choroidal vasculature extraction images 556, 566. The RG color fundus images 554, 564, ICG, and OCTA are each also not limited to 2D representations, and may be displayed in 3D representations. Images displayed in the latest image display field 550 and the previous image display field 560 may be selected from a displayed menu by switching switch display icons 558, 568 ON.

The follow-up observation field 570 displays changes to a specific region 12V3A of the RG color fundus images 554, 564 and to a specific region 12V3B of the choroidal vasculature extraction images 556, 566 in time series. The follow-up observation field 570 includes a latest image display field 576 for displaying the latest image of each of the specific regions 12V3A, 12V3B, a previous image display field 574 for displaying a previous image that is an image imaged prior to the latest image of each of the specific regions 12V3A, 12V3B, and a two-previous image display field 572 for displaying an image imaged prior to the previous image of each of the specific regions 12V3A, 12V3B (the fundus image imaged on Jan. 16, 2019 in FIG. 9). Below this is a time series blood vessel diameter display section 578 in which changes to the blood vessel diameters of the bulge portion 12E3 and the peripheral portion (line shaped portion 12V3) are displayed for the imaging times of each of the latest image, previous image, and two-previous image. In FIG. 9 three images that were imaged at three timings, latest, previous, and two-previous, are displayed in the follow-up observation field 570, however, there is no limitation to three images, and four or more fundus images imaged at different dates and times may be displayed in a time series.

Figure 10:
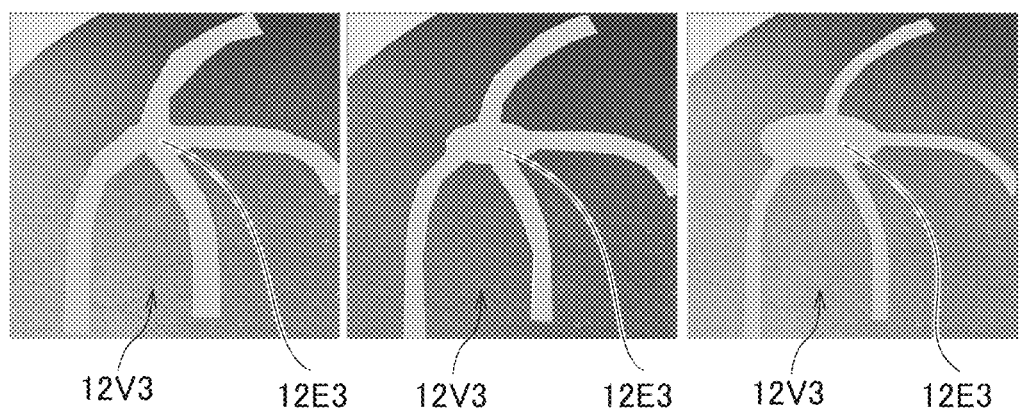
FIG. 10 is a schematic diagram illustrating a case in which choroidal vasculature extraction images of a specific region 12V3B have been combined with RGB color fundus images of the specific region 12V3A having the same respective imaging date, displayed in a time series in a follow-up observation region 570.

FIG. 10 is a schematic diagram illustrating cases in which the respective RG color fundus images of the specific region 12V3A displayed in time series in the follow-up observation field 570 are combined with the respective choroidal vasculature extraction images of the specific region 12V3B having the same imaging dates. A combined image such as that of FIG. 10 may be displayed in the follow-up observation field 570.

Figure 11:
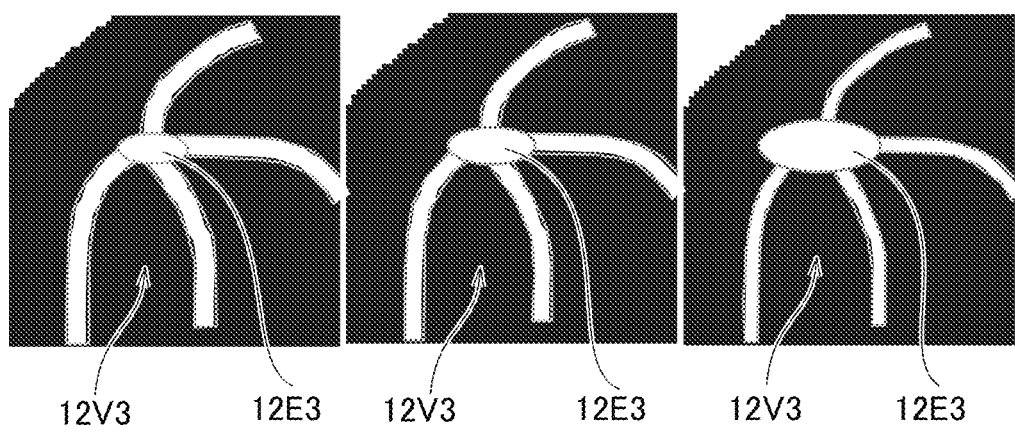
FIG. 11 is a schematic diagram illustrating a case in which outline emphasis images extracted from RGB color fundus images of a specific region 12V3A have been combined with choroidal vasculature extraction images of a specific region 12V3B having the same respective imaging date displayed in a time series in a follow-up observation region 570.

FIG. 11 is a schematic diagram illustrating a case in which outline emphasis images extracted from the RG color fundus images of the specific region 12V3A are combined with the choroidal vasculature extraction images of the specific region 12V3B of the same imaging date displayed in time series in the follow-up observation field 570. A combined image such as that of FIG. 11 may be displayed in the follow-up observation field 570. The image displayed in the follow-up observation field 570 can be selected from a displayed menu by switching a switch display icon 582 ON. The outline emphasis image can be generated by applying a well-known method such as a Sobel filter to an RG color fundus image or a choroidal vasculature extraction image. Combining the outline emphasis image with a choroidal vasculature extraction image, which is a binarized image, enables the line shaped portion 12V3 and the bulge portion 12E3 of the choroidal vasculature to be ascertained even more clearly than with a binarized image. Moreover, by changing the color of the outline sections in the outline emphasis image at the line shaped portion 12V3 and the bulge portion 12E3, the line shaped portion 12V3 and the bulge portion 12E3 can be clearly discriminated.

As explained above, in the present exemplary embodiment the line shaped portions of the choroidal vasculature are emphasized in the analysis image by the line emphasis processing, and the line shaped portions of the choroidal vasculature can be selectively extracted by binarization of the image.

Moreover, in the present exemplary embodiment the bulge portions of the choroidal vasculature can be selectively extracted by performing binarization processing on the analysis image or by detecting convex portions in the analysis image using a Hessian matrix.

The choroidal vasculature and vortex veins can be reliably extracted from a fundus image by the extraction of line shaped portions and bulge portions of the choroidal vasculature according to the present exemplary embodiment. This enables the choroidal vascular network including the vortex veins to be digitalized, and various analyses to be performed thereon. For example, prompt detection of signs of arterial sclerosis is facilitated, and an ophthalmologist is able to predict disorders related to vascular disease.

It must be understood that the image processing of the respective exemplary embodiments described above is merely an example thereof. Obviously redundant steps may be omitted, new steps may be added, and the processing sequence may be swapped around within a range not departing from the spirit of technology disclosed herein.

Although explanation has been given in the respective exemplary embodiments described above envisaging an example in which a computer is employed to implement image processing using a software configuration, the technology disclosed herein is not limited thereto. For example, instead of a software configuration employing a computer, the image processing may be executed solely by a hardware configuration such as a field programmable gate array (FPGA) or an application specific integrated circuit (ASIC). Alternatively, a configuration may be adopted in which some processing out of the image processing is executed by a software configuration, and the remaining processing is executed by a hardware configuration.

The invention claimed is:

1. An image processing method comprising:
acquiring a fundus image;
extracting a line-shaped portion from a first processing image generated by line emphasis processing on the fundus image and followed by binarization processing;
extracting a lump-shaped portion from a second processing image generated by binarization processing on the fundus image; and
generating a combined image in which the extracted the line-shaped portion from the first processing image and the extracted the lump-shaped portion from the second processing image are combined.

2. The image processing method of claim 1, wherein:
the line-shaped portion is a line-shaped portion of blood vessel; and
the lump-shaped portion is a lump-shaped portion of blood vessel.

3. The image processing method of claim 1, wherein the fundus image is a red-light capture image imaged with red light.

4. The image processing method of claim 3, wherein the fundus image is a binarized fundus image resulting from performing binarization processing on the red-light capture image.

5. The image processing method of claim 1, wherein the combined image is an image indicating vasculature structure of a fundus.

6. The image processing method of claim 1, wherein the combined image is an image indicating vasculature structure of a choroid of a fundus.

7. The image processing method of claim 1, wherein the line-shaped portion is a line-shaped area-portion of choroidal vasculature, and the lump-shaped portion is a lump-shaped portion of choroidal vasculature.

8. The image processing method of claim 7, wherein the line-shaped portion is a line-shaped portion of a vortex vein, and the lump-shaped portion is a vortex vein bulge portion.

9. The image processing method of any one of claim 1, wherein the line emphasis processing including discriminating that a local structure in the fundus image is a line.

10. The image processing method of any one of claim 1, wherein extracting the lump-shaped portion including extracting an area of a specific number of contiguous pixels having a specific luminance value as the lump-shaped portion.

11. An image processing method comprising:
acquiring a fundus image;
extracting a line-shaped portion of vasculature from a first processing image generated by line emphasis processing on the fundus image and followed by binarization processing;
extracting a lump-shaped portion of vasculature from a second processing image generated by binarization processing on the fundus image; and
integrating an image of the extracted line-shaped portion from the first processing image together with an image of the extracted lump-shaped portion from the second processing image to generate a vascular image in which blood vessels have been made visible.

12. The image processing method of claim 11, wherein the fundus image is a grayscale image, and the vascular image is a binarized image.

13. The image processing method of claim 11, wherein the vascular image is a choroidal vascular image in which a choroidal vasculature has been made visible.

14. The image processing method of claim 13, wherein the line-shaped portion is a line-shaped portion of the choroidal vasculature.

15. The image processing method of claim 13, wherein the lump-shaped portion is a bulge portion of the choroidal vasculature.

16. An image processing method comprising:
- acquiring a fundus image including a choroidal vasculature;
- extracting a line-shaped portion of choroidal vasculature from a first processing image generated by line emphasis processing on the fundus image;
- extracting a lump-shaped portion of choroidal vasculature from a second processing image generated by binarization processing on the fundus image; and
- integrating an image of the extracted line-shaped portion from the first processing image together with an image of the extracted lump-shaped portion from the second processing image to generate a choroidal vascular image configured by the line-shaped portion and the lump-shaped portion.

17. The image processing method of claim 16, wherein the fundus image is an image acquired by a scanning laser ophthalmoscope.

18. The image processing method of claim 16, wherein the fundus image is a face-on image by an angiographic method using optical coherence tomography.

* * * * *